US005512280A

United States Patent [19]

Johal et al.

[11] Patent Number: 5,512,280

[45] Date of Patent: Apr. 30, 1996

[54] MAINTENANCE AND LONG TERM STABILIZATION OF FUNGAL CONIDIA USING SURFACTANTS

[75] Inventors: Sarjit S. Johal, Hopkinton; Lorraine M. Marold, Worcester, both of Mass.

[73] Assignee: EcoScience Corporation, Northboro, Mass.

[21] Appl. No.: 329,472

[22] Filed: Oct. 26, 1994

[51] Int. Cl.[6] .............................. C12N 1/14; C12N 1/04; A01N 63/04

[52] U.S. Cl. ....................... 424/93.5; 435/260; 435/254.1

[58] Field of Search ................................ 435/254.1, 260; 424/93.5

[56] References Cited

U.S. PATENT DOCUMENTS

| | | | |
|---|---|---|---|
| 2,176,423 | 10/1939 | Jaeger . | |
| 4,008,351 | 2/1977 | Inoue et al. | 424/26 |
| 4,246,258 | 1/1981 | Ayers et al. | 424/115 |
| 4,877,617 | 10/1989 | Namikoshi et al. | 424/409 |
| 4,885,310 | 12/1989 | Kern | 514/547 |
| 4,925,663 | 5/1990 | Stimac | 435/911 |
| 4,959,268 | 9/1990 | Hagiwara et al. | 428/403 |
| 5,057,315 | 10/1991 | Gunner et al. . | |
| 5,057,316 | 10/1991 | Gunner et al. . | |
| 5,288,634 | 2/1994 | Harman et al. | 435/254.1 |

FOREIGN PATENT DOCUMENTS

| | | |
|---|---|---|
| 2255018 | 10/1992 | United Kingdom . |
| WO93/24013 | 12/1993 | WIPO . |

OTHER PUBLICATIONS

Derwent Abs. 94–183915/22 2A9304811—(Mar. 30, 1994) Grigas et al.

Angus, T. A. and P. Luthy, "Formulationof Microbial Insecticides: III, Liquid Formulations, " *Microbial control of Insects and Mites,* Academic Press, Ed., 626–628 (1971).

Boucias, D. G., et al., "Nonspecific Factors Involved in Attachment of Entomopathogenic Deuteromycetes to Host Cuticle," *App. and Env. Micro.* 54(7):1795–1805 (1988).

Daoust, Richard A., et al., "Effect of Formulation on the Viability of *Metarhizium anisopliae* Conidia," *J. Inver. Pathol.* 41:151–16 (1983).

Daoust, Richard A., and Donald W. Roberts, "Studies on the Prolonged Storage of *Metarhizium anisopliae* Conidia: Effect of Temperature and Relative Humidity on Conidial Viability and Virulence against Mosquitoes," *J. Inver. Path.* 41:143–150 (1983).

Daoust, Richard A. and Donald W. Roberts, "Studies on the Prolonged Storage of *Metarhizium anisopliae* conidia: Effect of Growth Substrate on Conidial and Virulence against Mosquitoes," *J. Inver. Path.* 41:161–170 (1983).

Dillon, Roderick James and Anthony Keith Charnley, "A technique for accelerating and synchronising germination of conidia of the entomopathogenic fungus *Metarhizium anisoplae*" *Arch. Microbiol.* 142:204–206 (1985).

Ferron, P., "Biological Control of Insect Pests by Entomogenous Fungi," *Ann. Rev. Entomol.* 23:409–442 (1978).

Reinecke, P., et al., "A New Microbial Insecticide for Use in Horticultural Crops," *Brighton Crop Protection Conference—Pests and Diseases* 49–54 (1990).

Roberts, Donald W. and Amy S. Campbell, "Stability of Entomopathogenic Fungi," *Entomol. Sci. Am.,* Miscellaneous Publications, 10:19–76 (1977).

Sandhu, S. S. et al., "Studies on Prolonged Storage of *Beauveria bassiana* Conidia: Effects of Temperatures and Relative Humidity on Conidial Viability and Virulence against Chickpea Borer, *Helicoverpa armigera,*" *Biocontrol Sci. and Tech.* 3:47–53 (1993).

Ward, Michael G., "Formulationof Biological Insecticides," *Advances in Pesticide Formulation Technology,* American Chemical Society, Ed., Chapter 13:175–184 (1984).

*Primary Examiner*—Herbert J. Lilling
*Attorney, Agent, or Firm*—Arnall Golden & Gregory

[57] ABSTRACT

A method for long term storage of a stable monodispersed aqueous suspension of conidia has been developed. This is based on the use of surfactants in a concentration range significantly higher than expected that is completely compatible with conidia, generally in the range of between 1 and 2% (w/v) in an aqueous suspension of between 0.01 and 50% (w/v) conidia. Fungal propagules (conidia) of entomopathogenic fungi such as *M. anisopliae* and *B. bassiana* can be successfully combined with higher than expected concentrations of commercially available anionic surfactants and wetting agents such as dioctyl sulfosuccinates (DSS) salts and derivatives thereof with no apparent negative impact upon either viability or insecticidal activity of the conidia. Other surfactants, dispersants and non-fungicidal materials can be added to the stabilized conidial suspensions without loss of viability, dispersibility, or shelf-life. Examples demonstrate the usefulness of these materials in the stabilization of conidial suspensions that remain viable and effective for the control of insects. The conidial formulations described in the examples can be applied in either dry or wet form.

28 Claims, 1 Drawing Sheet

MAINTENANCE AND LONG TERM STABILIZATION OF FUNGAL CONIDIA USING SURFACTANTS

BACKGROUND OF THE INVENTION

The present invention is generally in the field of biological formulations, in particular, methods for making stable and useful fungal conidial formulations.

A number of investigators have explored the possibility of using entomopathogenic fungi for insect biocontrol. The potential for successful application of entomopathogenic fungi as biological control agents has only recently begun to be developed. The successful commercial use of the biocontrol agents has required significant advances in a number of fundamental research areas including strain selection, bioassay procedures, process development, and in production related areas such as manufacturing, packaging and distribution.

The entomopathogenic fungi classified as Hyphomycetes are natural insect pathogens which have a biphasic biological cycle consisting of a mycelial vegetative phase and an asexual conidiospore reproductive phase. Since only the reproductive propagules, the conidia, are involved in the infective process, the conidia are the preferred material for use in biocontrol. The conidia infect a susceptible insect host through the integument. Three steps have been recognized in the development of the infection:

a) adhesion of the spore to the insect cuticle;

b) formation and penetration of the insect cuticle by the germ tube; and c) growth of the fungus within the insect body.

In one preferred method of insect control with entomopathogenic fungi, the fungus is applied in the form of a conidial dispersion or suspension. In another, the treatment involves storage and distribution of conidia in a chamber which is attractive to the insects. Problems are inherent in all methods of conidial application and the lack of suitable formulations and satisfactory delivery systems have not yet been fully overcome, limiting the large scale development of fungi as biological control agents.

In nature, the initial fungus-host interaction is by chance. The conidiospores of fungi such as *Metarhizium anisopliae* and *Beauveria bassiana*, among others, have evolved spore surface (or coat) physicochemical attributes which enhance and probably mediate the attachment of the spore to the insect cuticle. No pesticidal activity is possible in the absence of attachment and germination. Therefore, the role of process components which might affect attachment and germination by the conidia must be considered during the selection of the methodologies that might be used in any commercial development of fungal biocontrols. Any process or agent which adversely interferes with either the attachment or germination steps could render the conidia noninfective and therefore unacceptable for use in biocontrol applications.

In addition to good insecticidal activity, essential features of an acceptable fungal biological control product include extended shelf life, under a variety of temperature conditions, and adaptability to a variety of targeted applications. The instability of the fungal conidia in suspension can result in a loss of viability, or, if the conidia germinate, difficulty in spraying the conidia, as well as a loss of insecticidal activity.

The inability heretofore to successfully manipulate and control the microenvironment of the spore has severely limited the applicability of such conidia for commercial use. The lack of acceptable materials that do not adversely interfere with or suppress viability, attachment, or germination has been a major obstacle to the development of fungal-based biological control systems utilizing entomopathogenic fungi.

The conidia of many entomopathogenic fungi by virtue of their hydrophobicity are refractory to mixing and dispersion in aqueous diluents. Clearly, the development of stable, efficacious, water-based fungal biocontrol products with broad spectrum activity and extended shelf-life has been almost nonexistent. Many of these problems are a result of inadequacies of the current formulation technology with regard to any biocontrol agents, particularly fungal agents.

Surfactants, wetting agents and related compounds are known to facilitate the production of monodisperse suspensions of inert particles. In most nonbiological systems these additives are routinely employed to facilitate dispersion. In nonbiological systems, attributes such as performance, cost and application dictate selection. Moreover, even with biologics such as proteins, carbohydrates, lipids and mixtures where viability is not an issue, many different classes and concentrations of the agents can yield usable, functional commercial products. In contrast, living microorganisms require a very stringent and precise set of selection conditions where maintenance of viability, a preferred physiological state and functional biological activity are key requirements to be met. As a result of the unique needs inherent in living biological systems, few surfactants, wetting agents and related materials are known which perform satisfactorily, especially for commercial applications. Long term storage, maintenance of viability and high virulence are but a few of the required attributes for a commercial biological control product which have not been attainable heretofore with the known surfactants. Specifically, surfactants in general interfere with attachment and germination of conidia, and no stable aqueous formulations of conidia and surfactant are known since many fungi such as *M. anisopliae* and *B. bassiana* metabolize surfactants, detergents, wetting agents and similar materials. Within as brief a period as 72 hours, an aqueous suspension of conidia in the presence of known surfactants will germinate and grow to form a mycelial mass which is useless for commercial insect control.

In toto, the lack of usable surfactants, wetting agents and similar functional materials compatible with viable microorganisms such as entomopathogenic fungi has negatively impacted areas as diverse as laboratory research (assay development), manufacturing (processing aids), formulations and commercial applications. The concentrations of surface active agents which have been described in the literature as components of conidial suspensions has not exceeded 0.5 percent (volume to volume for liquids; weight to volume for solids), and the reported duration of exposure has been limited to just a few hours. Longer exposure results in either loss of viability or germination and growth of the conidia to form the vegetative mycelial morphology.

It is therefore an object of the present invention to provide materials useful in producing aqueous suspensions of viable, monodispersed conidia with pesticidal activity, stable to both long and short term storage.

It is a still further object of this invention to provide a conidia-compatible wetting agent for use in dry conidial formulations such as wettable (water-dispersible) granular powders and other formulations where a substantially water-based conidial suspension is required.

It is another object of the present invention to provide materials that exhibit antibacterial, but not antifungal activity, which do not inhibit germination after application or otherwise alter conidial viability, that are useful in preserving condia.

It is still another object of the present invention to provide materials that are useful in manipulating and controlling conidial viability and propagation.

SUMMARY OF THE INVENTION

A method and materials for long term storage of a stable monodispersed aqueous suspension of conidia have been developed. This is based on the use of surfactants in a concentration range significantly higher than expected that is completely compatible with conidia, generally in the range of between 1 and 2% (w/v) of surfactant in an aqueous suspension of between 0.01 and 50% (w/v) conidia. As demonstrated, fungal propagules (conidia) of entomopathogenic fungi such as *M. anisopliae* and *B. bassiana* can be combined with these higher than expected concentrations of commercially available anionic surfactants and wetting agents such as dioctyl sulfosuccinates (DSS) salts and derivatives thereof with no apparent negative impact upon either viability or insecticidal activity of the conidia. Subsequently, other surfactants, dispersants and non-fungicidal materials can be added to the stabilized conidial suspensions without loss of viability, dispersibility, or shelf-life.

Examples demonstrate the usefulness of these materials in the stabilization of conidial suspensions that remain viable and effective for the control of insects. The conidial formulations described in the examples can be applied in either dry or wet form. Insects that can be controlled or killed with the conidial formulation in either powder form or aqueous suspension include cockroaches, ants, termites, flies, wasps, mealworms, waxmoths, and corn root worms.

DETAILED DESCRIPTION OF THE INVENTION

I. Preparation of Stable Conidial Suspensions

Figure 1:
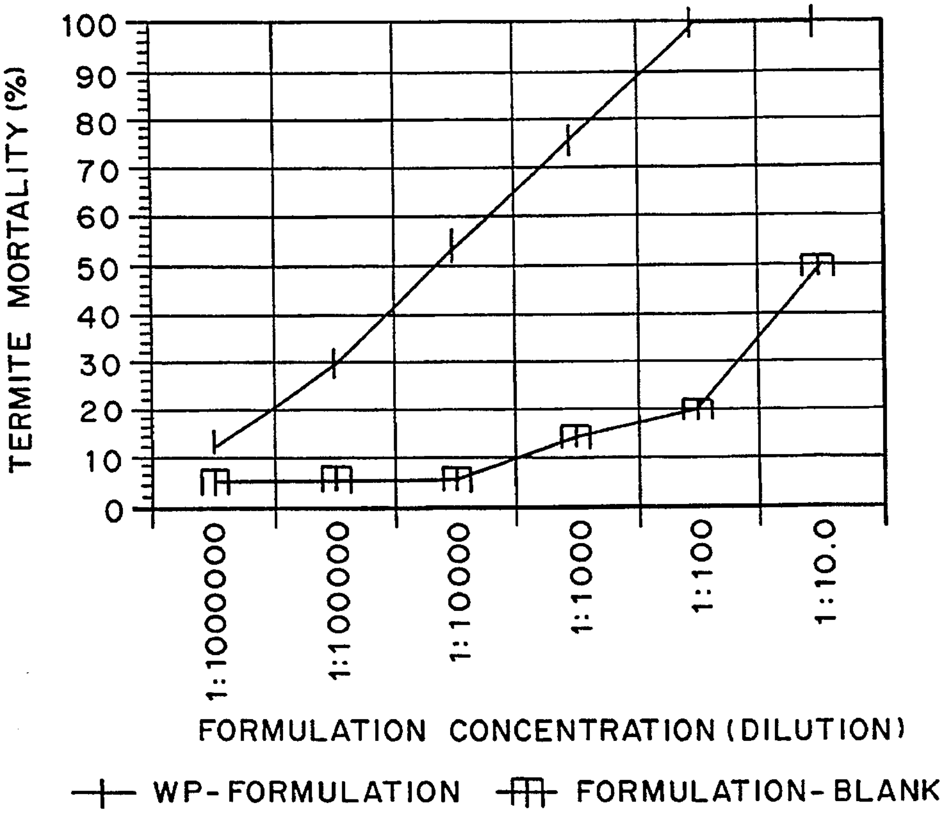
FIG. 1 is a graph of termite mortality versus formulation concentration.
Figure 2:
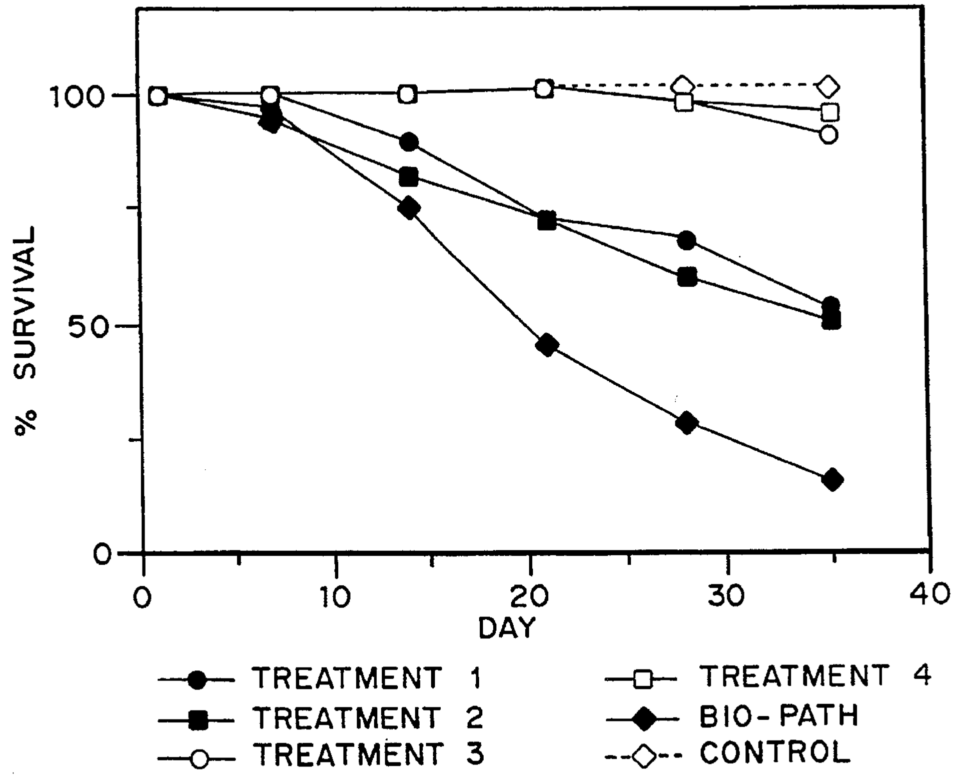
FIG. 2 is a graph of percent survival versus days.

Contrary to conventional wisdom, fungal propagules of entomopathogenic fungi such as *M. anisopliae* and *B. bassiana* can be successfully combined with higher than expected concentrations of commercially available anionic surfactants and wetting agents such as dioctyl sulfosuccinates (DSS) salts, sulfosuccinates and related chemical derivatives described in U.S. Pat. No. 2,176,423, and listed in McCutchens Vol. 1: Emulsifiers and Detergents Under the Chemical Classification of Sulfosuccinates and their Derivatives, the teachings of which are incorporated herein.

Advantages of formulations using various combinations of these surfactants include:

(a) the production of stable, discrete, monodispersed, aqueous suspensions for various applications and formulations, as required;

(b) the opportunity to vastly increase yields of harvestable conidia (by increasing dispersion and stripping) from natural and synthetic solid substrate fermentation matrixes;

(c) the potential to dry conidia in the presence of the materials to produce a dehydrated material which then can be reconstituted immediately and effectively to yield a monodispersed suspension; and (d) the ability to make further formulation improvements which might be difficult, if not impossible, in the absence of a stable, discrete, disperse biological active ingredient, for example, aqueous gels, soaps or shampoos containing fungal conidia as active ingredients.

1. Preparation of Fungal Conidia.

Conidia can be produced by any of the standard procedures such as culturing of the fungi on standard agar-based nutritive media formulations, solid state (substrate) fermentations on nutritive sources such as rice, barley, wheat, corn, other cereal grains or straw, and submerged fermentation. The purified or mixed conidia-mycelia and substrate combinations can be either used immediately (for example, post harvest) or recovered from ambient, humidified or dry storage conditions (as may be required, appropriate or preferred for maintenance of viability), suspended in water, oil or any mixture and combination thereof. The preferred physiological state is that with the highest percent viability and rapid germination rate. The most preferred state is purified, high viability, high pathogenic potential entomopathogenic fungi.

Entomopathogenic fungi are known to those skilled in the art and can be obtained from the American Type Culture Collection, 12301 Parklawn Drive, Rockville, Md. 20852 U.S.A., for a fee, or as isolates from infected insects, soil, or vegetation. Examples of entomopathogenic fungi include *Metarhizium anisopliae, Beauveria bassiana*, Verticillium and Paecilomyces species.

2. Selection of Surfactants

The surfactants which have been discovered to be fully compatible with entomopathogenic fungal conidia are those which permit the hydrophobic conidia (i.e., the conidia) to blend and form monodisperse suspensions in aqueous solutions.

In the preferred embodiment, the surfactants are sulfosuccinates and their derivatives, as described in U.S. Pat. No. 2,176,423, entitled "Esters of Sulphodicarboxylic Acids". The preferred surfactants are esters of sulpho saturated and unsaturated aliphatic dicarboxylic acids such as mono and disulphosuccinic, sulphochlosuccinic, sulphobromosuccinic, sulphoadipic, sulphopyrotartaric, sulphoglutaric, sulphosuberic, sulphosebacic, sulphobutylsuccinic, sulphobenzylsuccinic, sulphomaleic, sulphofumaric, sulphodimethylsuccinic, sulphomethylglutaric, sulphopimelinic, sulphopropylsuccinic, sulpho-octylglutaric, sulphobenzylmalonic, and other sulphonated dicarboxylic acids of the aliphatic series. Currently, the most preferred commercially available surfactant is Aerosol O.T.™ from Cytec Industries. The various commercially known materials include: Aerosol™ (Cytec Industries), Atlas™ (Atlas Refinery, Inc.), Fizul™ (Finetex, Inc.), Mackanates™ (The Mcintyre Group Ltd.), Pentex™ (Rhone-Poulenc Inc.), Alconate Chemax DOSS™ (Chemax Inc. ), Gemtex™ (Finetx, Inc.), Miranate Protowet™, Alkasurf SS Cyclopol™, Hodag™ (Hodag Chemical Company), Monamate LA-100™, Monamate CPA-100™, Monamate OPA-100™ and Monamate LNT-40™ (Mona Industries Inc.), Schercopol™ (Scher Chemicals), Alrowet™, Denwet™ (Graden Chemical), Hostapol™, Standapol™ (Henkel Corporation), Arylene™ (Hart Chemical Ltd.), Eccowet W-50™ (Eastern Color & Chemical Co.), Incrosuls™ (Croda, Inc.), Sulfotex, Astromid, Emcol™, Jordawet, Texwet™ (Intex Chemical), Astrowet™ (Alco Chemical Corp.), Emery, Karawet, Nekal, Thorowet™ (Clough Chemical), Varsulf™ (Sherex Chemical Co., Inc.), Complemix 100™ (American Cyanamid), Docusate Sodium (USP; Dioctyl Sodium Sulfosuccinate DSS, Docusate Sodium USP (50 percent) in PEG 400NF, Docusate K USP, 70 percent Free Flowing (mixture), Docusate Calcium (USP; 50 percent in Corn Oil NF (Ethanol) with Colloidal Silicone Dioxide), DKS Free Flowing Docusate K (USP; 70 percent).

It has now been discovered that these surfactants can be employed at concentrations heretofore deemed incompatible with the biological activity of fungal biological control agents, i.e., in concentrations of greater than between approximately 1 and 2% weight/volume (w/v) or volume to volume (v/v).

3. Preparation of Surfactant-Conidial Mixtures

The surfactant can be mixed with the conidia in either a dry or wet formulation. The dry formulation can consist of either an unhydrated surfactant and dry conidia blend or dry conidia coated with surfactant. Since water-dispersible granule formulations are produced by processing mixtures of the conidia with a wetting agent and a dispersant, the latter agents can either be mixed with the conidia and then the entire suspension brought to dryness or added to the solution first and dry conidia added thereafter.

The sequence of component additions to produce the final conidiospore formulations is not critical. Specifically, (1) the surfactant(s) can be dissolved in the aqueous solution prior to the addition of the conidia, (2) the conidia and surfactant(s) can be added and mixed concurrently with the aqueous solution or (3) the surfactant can be added to the water immediately after the addition of the conidia. Since the conidia of most entomopathogenic fungi are hydrophobic and aggregate at the aqueous solution interface, the preferred order of addition is to add conidia to the surfactant(s) containing solution. The least preferred sequence of addition is to add water to conidia then add surfactant(s).

The conidia are added to an aqueous solution containing the preferred surfactant(s) to produce an aqueous suspension which can range in concentration from 0.01 percent (w/v) to 90 percent (w/v) conidia. The final surfactant concentration used will depend on the final product formulation required. In the simplest case of an aqueous solution, the concentration of the surfactant employed will be dictated primarily by its respective solubility. For example, Dioctyl Sodium Sulfosuccinate (DSS) has a maximum solubility in water of about 1.5 to 2.0 percent (weight per volume). However, in more complex systems where other materials are incorporated, such as oils, alcohols, organic solvents and other materials required for formulations, the solubility of the surfactant will be affected. Consequently, the classes of surfactant(s) at the higher concentrations, between about 2.5 percent to about 80 percent, in combination with aqueous additives, are still fully compatible with the conidiospores so long as the additives themselves either separately or combined do not adversely affect the conidia.

Surfactants added to the conidia at a concentration in the range of between 0.001 percent to 100 percent (weight to volume), more preferably between 0.2 to 20 percent (weight to volume), and most preferably between 0.5 to 5 percent (weight to volume), will inhibit the anomalous growth of undesirable mycelia and thereby improve the quality of a resultant conidial product without adversely affecting viability and insecticidal activity.

The aqueous surfactant-conidial suspensions can be stored for long periods, generally more than six months, as dispersed, active suspensions with complete maintenance of insecticidal activity. The aqueous suspensions can be further processed to yield other compositions containing conidia as the active ingredient, for example, conidial powders, cakes, granules, gels and shampoos, which previously could not have been made.

4. Other Formulation Additives

Other surfactants and functional formulation additives which are deficient in certain respects, for example, those which serve as substrate to promote mycelial growth if used alone, but which are compatible with conidiospores including different groups of nonionic, anionic and cationic surfactants and oils, can now be effectively stabilized and formulated at the required concentrations in combination with this group of surfactants as long as an effective amount of surfactant of the type described above is added to the conidiospores.

II. Manipulation of Growth of Conidia.

In the presence of the sulfosuccinate surfactants, conidial viability is maintained over months in a preferred, stable physiological state. More specifically, germination and subsequent growth are not triggered in aqueous solutions containing the sulfosuccinated surfactants. The conidia retain complete functional biological and insecticidal activity. The preferred surfactants also exhibit antibacterial activity when added to the conidia at the appropriate concentrations. This antibacterial activity significantly enhances the utility of formulations employing the agents by eliminating potential bacterial contamination problems during production, storage and use without the addition of other preservative(s) or bacteriostatic agents.

These materials can be used to differentially affect or modulate the growth characteristics of fungal propagules. For example, materials can be used which exhibit differential effects upon conidia and hyphae. The surfactants can also be used for the controlled growth of hyphae in solid support environments. When fungi are grown in situ on solid matrixes, for example, agar, gelatin, cereal grains, films and other natural materials or synthetic matrixes such as foams, fabrics, nets, and screens, the mycelia grow to cover the surface of the matrix and subsequently conidiate. Under a variety of environmental conditions, however, the mycelia often continue to grow and/or the conidia produced germinate and grow to yield mycelia within the conidial lawn or at the periphery. This secondary mycelial growth compromises conidial uniformity as well as quality of harvested yields by introducing hyphal impurities and potentially presenting biochemically and physiologically different subpopulations of conidia. The resultant disparate conidiospore subpopulations may differ, for example, in pathogenic potential and infection characteristics, which could result in a conidial formulation with reduced pathogenic potential. The ability of these surfactants to differentially inhibit mycelial growth without adversely impacting conidial viability and insecticidal activity allows one to successfully control the growth of the fungal mycelia in a selected and preferred manner and to formulate conidia into gels, shampoos, dry pellets, cakes, soaps, and other combinations.

The present invention will be further understood by reference to the following non-limiting examples.

EXAMPLE 1

Preparation of Surfactant-Conidial Formulations

*M. anisopliae* was grown on nutritive agar plates for the production of conidia for all three treatments described in this example. The conidia were used without further treatment except where noted.

Treatment 1. Heavily sporulated cultures stored at room temperature were harvested by brushing conidia from the surface. Conidia were transferred to bottles with screw-cap closures containing 100 milliliters of sterile distilled water in an amount sufficient to produce a 10 percent (weight to volume) conidial suspension. Immediately thereafter, dioctyl sulfosuccinate (DSS) was added to yield a final concentration of about 1.0 to 1.25 percent (weight to volume). The bottles were then vigorously shaken to concurrently facilitate dissolution of the surfactant and uniformly disperse the conidia. The conidia appeared uniformly dispersed almost immediately upon addition of the surfactant. The capped bottles were then stored at room temperature and the conidial contents tested by the germination assay which is described below.

Treatment 2. Treatment 1 was modified by pretreating the conidia with an oil. The oil pretreated conidia were then transferred to the surfactant solutions as described above. The treated samples were then stored and assayed as described in Treatment 1.

Treatment 3. This treatment was identical to Treatment 2 above except that no surfactant was added to the oil-pretreated conidia-water combination.

Germination Assays: Conidia were brushed onto potato-dextrose-agar (PDA) plates which were previously sectored into quadrants. The plates, inoculated in duplicate, were then incubated for a total of 13 hours at 28° C., 75 percent relative humidity before conidia were observed microscopically (200×). A minimum of two hundred conidia were examined from each of two sectors from each of the two plates. Conidia were then scored for the presence or absence of germ tubes from which data average percent germination was determined. It should be noted that for all treatments (1–3) conidia were examined for germination prior to incubation to assure the absence of premature germination which might give rise to a false positive result.

Insect Bioassay: After about four and a half months of storage at room temperature, the conidia-surfactant suspensions from Treatments 1 and 2 were diluted with water to produce a suspension of about $10^5$ conidia per milliliter. The diluted suspensions were then used to treat wax moth larvae and mealworms. After treatment the insects were returned to their sterile environments. After seven days both the wax moth larvae and the mealworms were examined for mortality (Tables 1 and 3 respectively). After recording the observations, the treated insects were retained for an additional six days and then scored for conidiation of the cadavers (Tables 2 and 4 for wax moth larvae and mealworms respectively).

The results demonstrate that DSS at a concentration of about 1.25 percent (weight per volume) did not adversely affect conidial viability after about four months storage at room temperature. Table 1 shows the viabilities of the conidia following various treatments. Treatments 1 and 2 displayed the highest viabilities at about four months whereas dry untreated conidia from the same batch yielded a slightly lower percent germination. Some of the oil-treated conidia without surfactant, i.e., Treatment 3, germinated in the water prior to assay. Therefore, conidia from Treatment 3 could not be assayed.

TABLE 1

Germination of *M. anisopliae* Conidia
Stored in DSS (1.2 percent at room temperature and dry).

| | AVERAGE PERCENT GERMINATION TIME (DAYS) | | | | | |
|---|---|---|---|---|---|---|
| CONDITIONS | 3 | 16 | 34 | 36 | 49 | 113 |
| OIL PRETREATMENT | 41 | 91 | ND (1) | ND | 97 | 94 |
| NO OIL TREATMENT | 56 | 86 | 74 | 89 | 93 | 91 |
| DRY CONIDIA | 57 | 59 | ND | 90 | 74 | 79 |

(1) Not Done.

The results of the insect bioassay are shown in Tables 2, 3, and 4. As shown by a comparison of the results of mortality (Table 2) and conidiation (Tables 3 and 4), there is a high correlation between the number of dead insects and the number of cadavers showing conidial growth. The growth resembles that of *M. anisopliae*, strongly suggesting that death was due to a systemic mycosis with this fungus. Treatment of conidia with the surfactant precludes germination in solution without subsequent loss of viability and/or infectivity for a susceptible insect host. The conidia in solution resulting from Treatments 1 and 2 were homogeneous and well dispersed. Specifically, the conidia appeared as single discrete entities rather than clumps. In contrast, conidia in water alone did not disperse well and formed non-wettable, film-like masses (monolayers) at the water/air interface.

TABLE 2

Mortality at 7 days of Wax Moth Larvae after Treatment with *M. anisopliae*
Conidial Suspensions containing DSS at 1.2 percent and stored for 4 months.

| | CONDITIONS | | | PERCENT MORTALITY BIOASSAY REPLICATE NO. | | | | |
|---|---|---|---|---|---|---|---|---|
| SAMPLE NO. | DSS | OIL OVERLAY | CONIDIA | 1 | 2 | 3 | 4 | 5 |
| 1 | PRESENT (P) | P | P | 100 | 100 | 100 | 100 | 80 |
| 2 | P | ABSENT (A) | P | 100 | 100 | 100 | 100 | 100 |
| 3 | A | A | P | 100 | 100 | 100 | 100 | 100 |
| 4 | A | A | A | 40 | 20 | 40 | 40 | 20 |
| 5 | P | A | A | 20 | 40 | 40 | 20 | 40 |

TABLE 3

Conidiation of Wax Moth Larvae Cadavers 13 days post challenge with Oil pretreated *M. anisopliae* Conidial Suspensions stored in DSS at 1.2 percent for 4 months.

| SAMPLE NO. | CONDITIONS DSS | OIL OVERLAY | CONIDIA | PERCENT CADAVERS CONIDIATED REPLICATE TRIAL NO. 1 | 2 | 3 | 4 | 5 |
|---|---|---|---|---|---|---|---|---|
| 1 | PRESENT (P) | P | P | 80 | 100 | 100 | 100 | 100 |
| 2 | P | ABSENT (A) | P | 100 | 100 | 100 | 100 | 100 |
| 3 | A | A | A | 0 | 0 | 0 | 0 | 0 |
| 4 | A | A | A | 0 | 0 | 0 | 0 | 0 |
| 5 | P | A | A | 0 | 0 | 0 | 0 | 0 |

TABLE 4

Conidiation of Mealworm Cadavers 13 days post challenge with oil pretreated *M. anisopliae* conidial suspensions stored in DSS at 1.2 percent for 4 months.

| CONDITIONS DSS | OIL OVERLAY | CONIDIA | PERCENT CADAVERS MORTALITY REPLICATE TRIAL NO. 1 | 2 | 3 | 4 | 5 |
|---|---|---|---|---|---|---|---|
| PRESENT (P) | P | P | 40 | 100 | 100 | 100 | 100 |
| P | ABSENT (A) | P | 100 | 100 | 100 | 100 | 100 |
| A | A | P | 100 | 80 | 100 | 100 | 100 |
| A | A | A | 0 | 0 | 0 | 0 | 0 |
| P | A | A | 0 | 0 | 0 | 0 | 0 |

EXAMPLE 2

Comparison of Effect of Surfactants on Conidial Viability.

*M. anisopliae* was grown on nutritive-based agar plates for the production of conidia for all the treatments described in this example. The conidia were used without further treatment. After harvesting, the conidia were suspended in water using vigorous agitation at a concentration of about ten percent (weight per volume). Three milliliters of conidial suspension were then added to achieve a final spore density of about $2\times10^7$ per milliliter in a series of bottles with screw-cap closures containing the following additives: (a) dioctyl sulfosuccinate at one percent (weight per volume); (b) alkoxylated alcohol at 0.5 percent and 1 percent (volume per volume) and (c) distilled water with no additives. All of the bottles were capped, vigorously shaken, then stored at room temperature.

Germination assays were performed on the conidial suspensions after five, twelve and nineteen days, as described in Example 1. Conidia were also examined immediately after plating to ensure that conidia had not germinated prematurely during storage. The results are shown in Table 5.

TABLE 5

Germination of *M. anisopliae* Conidia Following Storage in Selected Surfactants at Room Temperature.

| SURFACTANT | CONCENTRATION | AVERAGE PERCENT GERMINATION TIME (DAYS) 5 | 12 | 19 |
|---|---|---|---|---|
| DSS | 1 | 90 | 86 | 77 |
| | 1 | 91 | 81 | 58 |
| Alkoxylated Alcohol | 0.5 | 98 | G (1) | G |
| | 1 | 86 | G | G |
| Control | 0 | 98 | G | G |
| | 0 | 98 | G | G |

(1) Growth

The results support the following conclusions: Conidia treated with dioctyl sulfosuccinate at a concentration of one percent (weight per volume) in water (Table 5) did not germinate in suspension over a period of nineteen days. However, more than half of the conidia showed the ability to germinate when tested using the standard thirteen hour germination assay. Samples containing alkoxylated alcohol (b) and control (c), both showed visible fungal growth in situ after twelve days of storage at room temperature.

DSS at one percent (weight per volume) allowed for the stable storage of conidia with an acceptable germination profile. In contrast, diluent with either alkoxylated alcohol or water alone yielded unstable conidial suspensions, i.e., hyphal outgrowth from conidia was observed after only twelve days of storage.

EXAMPLE 3

Effect of Dehydration

Twenty milliliters of conidia-containing solution from Example 1, Treatment 1, were placed in a sterile petri dish. The dish was then placed in a biocontainment hood with the blower "on" for about 60 hours to accelerate dehydration. The laminar air flow resulted in evaporation of the water to produce conidia embedded in a dry, waxy matrix in the dish. Reconstitution of the matrix to the original volume, i.e., twenty milliliters, redissolved the matrix and uniformly resuspended the conidia.

The viability of the dried then rehydrated conidia was about 33 percent, as shown in Table 6. The ability to gradually rehydrate a surfactant-containing conidial suspension under accelerated ventilation conditions while simultaneously retaining viability of the conidia shows that direct concentrated surfactant-conidia interaction is not harmful.

TABLE 6

Germination of *M. anisopliae* Conidia after Rehydration and Reconstitution in the Presence of DSS at 1.2 percent.

| | Rehydration (days) AVERAGE PERCENT GERMINATION | | |
|---|---|---|---|
| CONDITIONS | <1 | 2 | 15 |
| DEHYDRATED/RECONSTITUTED SUSPENSION | 13 | 30 | 33 |
| UNMODIFIED SUSPENSION | 74 | 89 | 93 |
| DRY CONIDIA | ND (1) | 90 | 74 |

(1) Not Done

EXAMPLE 4

Effect of Surfactant on Germination.

*M. anisopliae* was grown on nutritive-based agar plates for the production of conidia. After about twelve days, the mature heavily sporulated cultures were harvested. Untreated conidia from three different batches (Samples 1–3) were stored under ambient conditions for a period of about ten days to facilitate drying. Conidia at a concentration of about 1 percent (weight to volume) were then placed in tubes with screw-cap closures containing either distilled water or DSS, at a concentration of about 0.5 percent (weight per volume). The solutions were sufficiently agitated to effect dispersal. The conidial suspensions were then allowed to equilibrate at room temperature for about one hour before testing. Germination was determined using a standard germ tube test procedure described above.

The results shown in Table 7 reveal that the three different conidial samples, when untreated (i.e., dry), had an average percent germination in the range of 74 to 95. Conidia exposed to an aqueous solution containing an anionic surfactant at a concentration of 0.5 percent (weight to volume) yielded average percent germination ranging from 63 to 99 percent. Conidia exposed to water alone showed activities in the range of 93 to 98 percent germination. However, the conidia added to water alone did not disperse sufficiently to produce a homogeneous suspension. The extreme hydrophobicity of the conidia precluded the production of a homogeneous suspension when conidia were added to water alone. By contrast, the conidia added to water in the presence of surfactant appeared to be uniformly monodispersed.

TABLE 7

Percent Germination of Conidial Samples of *M. anisopliae* After Exposure to DSS Surfactant Solution at 0.5 Percent.

| TREATMENT | SAMPLE NO. | PERCENT GERMINATION |
|---|---|---|
| DSS at 0.5 Percent | 1 | 99 |
| (weight per volume) | 2 | 95 |
| | 3 | 63 |
| Water | 1 | 98 |
| | 2 | 97 |
| | 3 | 93 |
| Dry Conidia | 1 | 86 |
| | 2 | 95 |
| | 3 | 74 |

The results demonstrate that DSS at a concentration of about 0.5 percent (weight per volume) did not adversely affect germination results. The exposure of conidia to the surfactant solution prevented undesirable properties of aggregation and biofilm formation. The conidia in the surfactant containing solution were homogeneously dispersed with no adverse effect as determined by the germination assay test results.

EXAMPLE 5

Effect of Surfactant on Long Term Storage and Germination.

Conidia of *M. anisopliae* were harvested from nutritive agar plates by dislodging the conidia from the surface with a brush. A stock solution of DSS at 1.5 percent (weight per volume) was sterilized by filtration. A series of 2-fold dilutions of the stock solution were prepared with sterile water diluent yielding 20 milliliters of DSS at concentrations of 1.5, 0.8, 0.4, 0.2 and 0.1 percent in sterile bottles with screw-cap closures. Each bottle of DSS solution was inoculated with conidia at the rate of one percent (weight per volume). A water control without surfactant was also inoculated as a control. Dry (i.e., untreated) conidia were added to a dry bottle as a nontreated control. All bottles with aqueous suspensions were vigorously shaken and then examined.

Conidial suspensions for all DSS concentrations tested appeared evenly distributed. In contrast, conidia in the water control sample were not wetted at all and resulted in the formation of a film on the water surface and extending up the walls of the bottle. The bottles were stored at room temperature for one hundred seventeen days (about 4 months). Germ tube tests were then performed on conidia stored under all conditions described according to the standard test described above. All plates were examined for the premature presence of germ tube formation.

No premature germ tubes were observed for any of the conditions. Average percent germinations as a result of the full tests were determined and are presented in Table 8. The data in Table 8 show that the conidia survived in high numbers, as indicated by germ tube results, ranging from 52 to 82 percent. Conidia in aqueous suspension alone yielded an average germination rate of 98 percent, whereas dry conidia alone yielded germination test results of only one percent.

TABLE 8

| Germination of *M. anisopliae* Conidia after Storage in DSS Solutions for 4 Months. | | |
|---|---|---|
| CONDITIONS | CONCENTRATION (W/V) | PERCENT GERMINATION |
| DSS | 1.5 | 74 |
| | 0.8 | 52 |
| | 0.4 | 84 |
| | 0.2 | 60 |
| | 0.1 | 82 |
| WET | — | 98 |
| DRY | — | 1 |

The results show that conidia in water resulted in a high germination rate with the disadvantages that, after nearly four months, the conidia were still not completely wetted. Dry conidia retained static charge-related effects such as clinging and airborne dispersion characteristics; dry untreated conidia did not survive with acceptable percentage yield; and the dry conidia exhibited undesirable aggregation associated with film formation.

In contrast, DSS in concentrations from between 0.1 to 1.5 percent (weight per volume) yielded quantifiable monodisperse suspensions of conidia free of film formation.

The results demonstrate that, from a commercial development standpoint, DSS in concentrations ranging from between 0.1 and 1.5 percent (weight per volume) was effective in satisfactorily maintaining long-term stability of *M. anisopliae* conidia in monodisperse aqueous suspensions.

EXAMPLE 6

Drying of Surfactant-Conidial Mixtures and Effect on Viability.

*M. anisopliae* conidia grown using standard procedures were harvested from nutritive agar trays. The harvested matter was then suspended in Aerosol-OT-100™, a DSS surfactant (0.4% weight per volume) (Monsanto Chemical Co., St. Louis, Mo.). The suspended conidia produced a homogeneous dark green, nearly black appearing liquid. The liquid was held at room temperature (22° C.).

Eight hundred milliliters of the liquid was poured into centrifuge bottles. The material was then centrifuged at 8,000 rpm (21° C.) for 15 minutes. The clarified supernatant was decanted. The soft frail pellet precluded the total removal of the supernatant fluid. Next, one hundred milliliters of distilled water was added to the bottle and the conidial pellet resuspended. The conidial suspension was poured into a shallow glass baking tray and positioned in a sterile culture hood. After about 72 hours in the hood the material exhibited a flake-like appearance with characteristic dry consistency.

About 22 grams of dry conidia 'flake' material was subcultured on agar media and found to be viable. This material was then placed in sterile petri dishes and stored in the dark at room temperature (about 22° C.) to determine the shelf-life/stability of the material.

Samples of the conidia were assayed for percent germination after about three weeks and again after six weeks in storage. The results of these assays are shown in Table 9.

TABLE 9

| Effect of DSS and storage on germination. | | |
|---|---|---|
| Sample Age | Percent Germination[1,2] | |
| (weeks) | 1 | 2 |
| 0 | ND | 88% |
| 3 | 83% | 82% |
| 6 | 36% | 54% |

[1]after treatment described in example
[2]if the standard germination assay is allowed to incubate for an additional 10 to 15 hours, the percent germination is increased to about 90–97% percent germination.

These results demonstrate that, even after six weeks, greater than about 90% of the conidia will germinate, albeit at a somewhat delayed rate.

EXAMPLE 7

Effect of the Presence of Surfactant on the Surface of Chambers for the Prevention of Undesirable Secondary Hyphal Outgrowth of *M. anisopliae.*

Plastic roach chamber assemblies were sprayed with ethanol at 70% v/v to sterilize the exterior surface. All traces of ethanol were removed by air drying the components under a biocontainment hood with the blower engaged. The chamber units were divided into five groups of four chambers. One group was treated with Aerosol OT™-70 PG (Cytec Industries) at 1.46% v/v in sterile water. The second group was treated with Aerosol OT™ identical to group 1 with the addition of Antifoam A (Sigma) added to the surfactant solution at 0.1% v/v. The third group was treated with only Antifoam A at a 0.1% v/v concentration and the fourth group was a control group treated with only sterile water.

Sterile nutritive agar plugs were cut from plates of nutritive agar media with a sterile metal test tube cap of 25 mm in diameter. One plug was placed in the bottom of each of the treated and untreated plastic chambers. The center of each agar plug was inoculated with *M. anisopliae* conidia. All four groups and a fifth group of untreated chambers were placed in plastic 4 mil bags with a cotton pad drenched with 10 ml of sterile water to provide for a humid environment. A sixth set of chambers was also tested without either sanitization or high humidity to determine the effect of these parameters on subsequent growth of the fungus.

All groups were then placed in an incubator at 25° C. at 95% relative humidity. The chambers were removed and examined for the presence of undesirable secondary hyphal outgrowth after 13 and 28 days of incubation. Results obtained from the various treatments in controlling the growth of *M. anisopliae* are shown in Table 10.

The results shown in Table 10 demonstrate that the use of conidial carriers prevents the growth and development of hyphae of *M. anisopliae* under conditions optimum for growth and sporulation of the fungi.

TABLE 10

| Effect of Carriers on Secondary Hyphal Growth. | | | | |
|---|---|---|---|---|
| | Incubation Time (in days) | | | |
| Treatment | 13 | 13 | 28 | 28 |
| Aerosol OT 70PG | A (absent) | A | A | A |
| Aerosol OT 70PG/ | A | A | A | A |

TABLE 10-continued

| Effect of Carriers on Secondary Hyphal Growth. | | | | |
|---|---|---|---|---|
| | Incubation Time (in days) | | | |
| Treatment | 13 | 13 | 28 | 28 |
| Antifoam A | | | | |
| Antifoam A | A | P (present) | P | P |
| With Water | P | P | P | P |
| No Water | P | P | P | P |
| Unsanitized/Untreated | P | P | P | P |

Modifications and variations of the present invention will be obvious to those skilled in the art from the foregoing detailed description. Such modifications and variations are intended to come within the scope of the appended claims.

We claim:

1. A conidial formulation comprising fungal conidia in combination with an anionic sulfosuccinate surfactant in a concentration of between 0.001 and 100% (weight surfactant/volume), wherein the surfactant inhibits germination of the conidia and is not metabolized or degraded by the fungus.

2. The formulation of claim 1 wherein the surfactant comprises esters of sulpho saturated and unsaturated aliphatic dicarboxylic acids.

3. The formulation of claim 1 wherein the concentration of surfactant is between 0.2 and 20% (w/v).

4. The formulation of claim 3 wherein the concentration of surfactant is between 0.5 and 5% (w/v).

5. The formulation of claim 2 wherein the concentration of surfactant is between 1 and 2% (w/v).

6. The formulation of claim 1 wherein the conidia is selected from the group consisting of Metarhizium and Beauveria fungi.

7. The formulation of claim 1 wherein the conidia and surfactant are mixed together in a dry form.

8. The formulation of claim 1 wherein the conidial formulation comprises a monodispersion of conidia in an aqueous solution containing surfactant.

9. The formulation of claim 1 further comprising material selected from the group consisting of cationic surfactants, oils, and nonionic and anionic surfactants which do not inhibit mycelial growth or are degraded by the conidia.

10. A method of making a conidial formulation comprising fungal conidia in combination with an anionic sulfosuccinate surfactant in a concentration of between 0.001 and 100% (weight surfactant/volume), wherein the surfactant is not degraded by the fungus and inhibits germination of the conidia, comprising mixing the conidia with the surfactant.

11. The method of claim 10 wherein the surfactant comprises esters of sulpho saturated and unsaturated aliphatic dicarboxylic acids.

12. The method of claim 10 wherein the concentration of surfactant is between 0.2 and 20% (w/v).

13. The method of claim 12 wherein the concentration of surfactant is between 0.5 and 5% (w/v).

14. The method of claim 13 wherein the concentration of surfactant is between 1 and 2% (w/v).

15. The method of claim 10 wherein the conidia is selected from the group consisting of Metarhizium and Beauveria fungi.

16. The method of claim 10 wherein the conidia and surfactant are in a dry form and are mixed together and added to an aqueous solution to adhere surfactant to the surface of the conidia.

17. The method of claim 10 wherein the conidia is dispersed in an aqueous solution containing the surfactant.

18. The method of claim 10 further comprising adding to the conidial-surfactant mixture a material selected from the group consisting of cationic surfactants, oils, and nonionic and anionic surfactants which do not inhibit conidial adhesion or germination.

19. A method for killing insects comprising administering to the insects an effective amount of a conidial formulation comprising fungal conidia in combination with an anionic sulfosuccinate surfactant in a concentration of between 0.001 and 100% (weight surfactant/volume), wherein the surfactant is not degraded by the fungus and inhibits germination of the conidia.

20. The method of claim 19 wherein the surfactant comprises esters of sulpho saturated and unsaturated aliphatic dicarboxylic acids.

21. The method of claim 19 wherein the concentration of surfactant is between 0.2 and 20% (w/v).

22. The method of claim 19 wherein the concentration of surfactant is between 0.5 and 5% (w/v).

23. The method of claim 20 wherein the concentration of surfactant is between 1 and 2% (w/v).

24. The method of claim 19 wherein the conidia is selected from the group consisting of Metarhizium and Beauveria fungi.

25. The method of claim 19 wherein the conidia and surfactant are in a dry form and are administered as a powder or dry dispersion.

26. The method of claim 19 wherein the conidial formulation comprises a monodispersion in an aqueous solution containing surfactant and is applied by spraying to the insects or the area they travel through.

27. The method of claim 19 further comprising administering with the conidia-surfactant mixture material selected from the group consisting of cationic surfactants, oils, and nonionic and anionic surfactants which do not inhibit conidial adhesion or germination.

28. The method of claim 19 wherein the insects are selected from the group consisting of cockroaches, ants, termites, flies, wasps, mealworms, waxmoths, and corn root worms.

* * * * *